United States Patent [19]

Altman et al.

[11] Patent Number: 4,464,175

[45] Date of Patent: Aug. 7, 1984

[54] MULTIPURPOSE TAMPONADE AND THROMBOSCLEROTHERAPY TUBE

[76] Inventors: Alan R. Altman, 1203 Buena Vista Dr.; Jorge G. Gutierrez, 544 Los Nietos, both of Palm Springs, Calif. 92262

[21] Appl. No.: 411,543

[22] Filed: Aug. 25, 1982

[51] Int. Cl.³ .................................................. A61M 25/00
[52] U.S. Cl. ............................................ 604/99; 128/4; 604/167
[58] Field of Search .................. 604/98, 99, 164, 167, 604/169, 102, 256, 100; 128/4, 6

[56] References Cited

U.S. PATENT DOCUMENTS

| | | | |
|---|---|---|---|
| 3,112,748 | 12/1963 | Colburn | 604/100 |
| 3,577,992 | 5/1971 | Merry | 604/99 |
| 3,818,903 | 6/1974 | Bleeker | 604/98 |
| 3,923,065 | 12/1975 | Nozick et al. | 604/102 |
| 4,301,811 | 11/1981 | Layton | 604/98 |
| 4,350,148 | 9/1982 | Sivak, Jr. et al. | 128/4 |

*Primary Examiner*—John D. Yasko
*Attorney, Agent, or Firm*—Richard A. Joel

[57] ABSTRACT

A multipurpose tamponade and thrombosclerotherapy tube for the endoscopic thrombosclerosis of esophageal varices and which permits effective gastric lavage at the same time that controlled esophageal tamponade is taking place. The invention comprises a tube-balloon assembly which includes a transparent polyvinyl tube of predetermined dimensions having a pair of opposing windows located at a spaced distance from its distal end. A latex balloon is mounted over the tube at an intermediate position and connected to a manometer by means of a polyvinyl catheter. The proximal end of the outer tube is connected to an irrigating system and a large siphon for gastric drainage. A metal cap fits snugly into the proximal outer tube and comprises a copper member having a latex nipple diaphragm mounted thereover which provides a seal and yet includes a small opening allowing passage of an endoscope.

12 Claims, 5 Drawing Figures

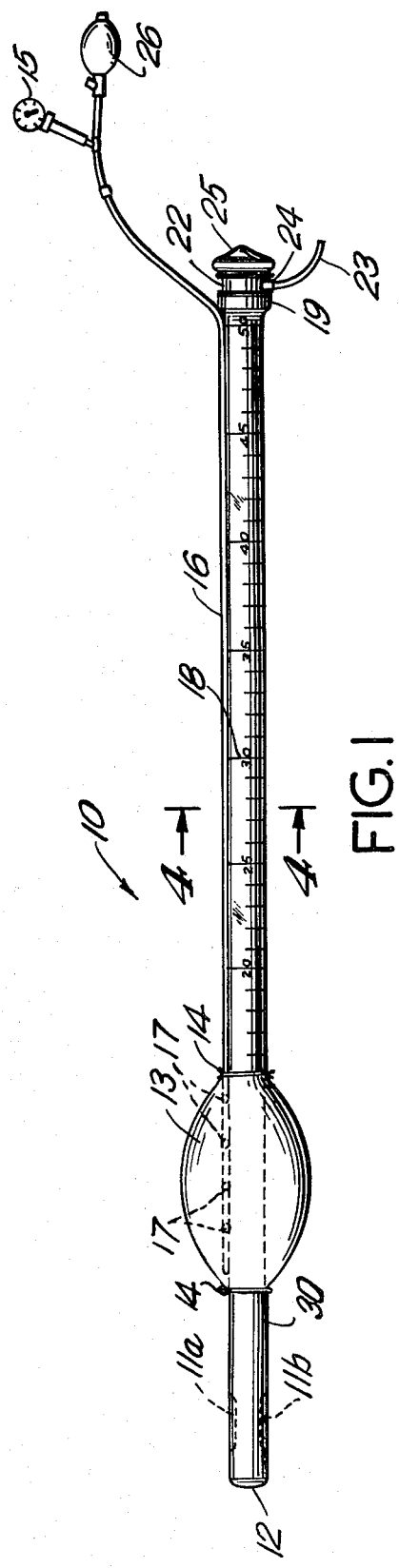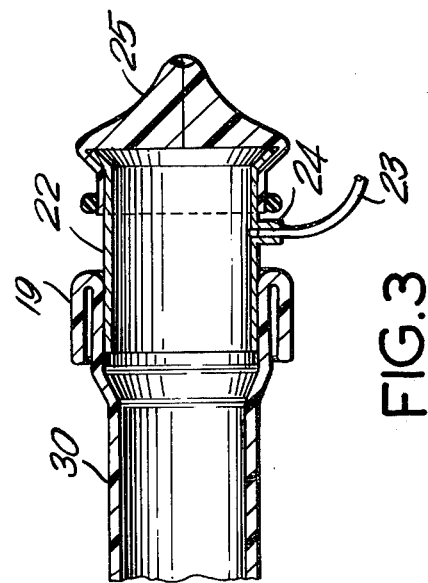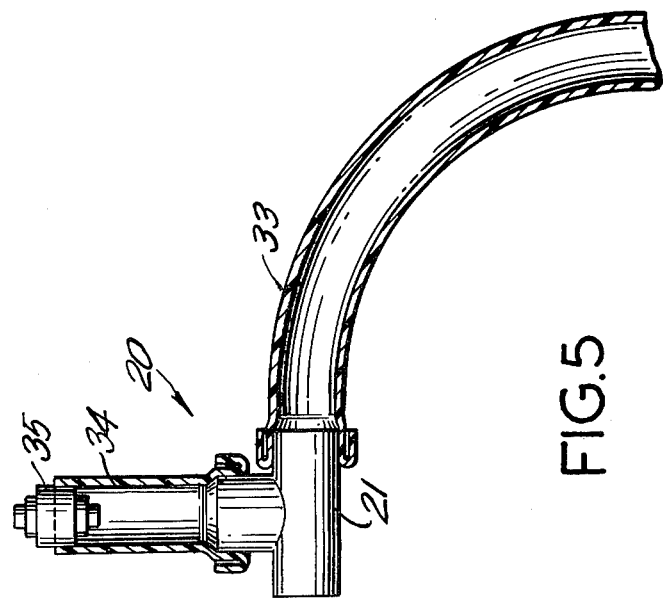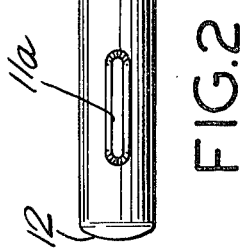

MULTIPURPOSE TAMPONADE AND THROMBOSCLEROTHERAPY TUBE

BACKGROUND OF THE INVENTION

This invention relates to medical instruments and particularly to a multipurpose tamponade and thrombosclerotherapy tube and the method of using same. The invention is uniquely effective for esophageal tamponade, simultaneous gastric lavage and endoscopic variceal sclerosis. While various individual elements of the invention may exist in the prior art, the unique combination of elements which comprise the invention and provide substantial advantages is nowhere disclosed in the prior art.

Among the prior art patents, U.S. Pat. No. 3,543,758 to McWhorter discloses an inflatable balloon-type catheter tube. While the McWhorter device discloses a retention balloon and an aperture adjacent its distal end, the patent does not disclose the proximal end structure of the invention, indeed the uses of the McWhorter device are quite restricted in scope. McWhorter U.S. Pat. No. 3,583,404 discloses a non-blocking irrigation catheter with drainage and irrigation lumens having means to prevent excessive fluid pressure buildup. The overall structure of the second McWhorter patent is considerably different from the present invention. The applications are similarly limited.

U.S. Pat. No. 3,593,713 to Bogoff et al discloses a catheter having a tubular body with an aperture at its forward end which is surrounded by a jacket having a fluid feed tube therein. The jacket includes a foraminous area adjacent its forward end for emission of fluid for direct treatment at the walls of a body orifice and an inflatable chamber is provided to retain a catheter in place. There is little similarity to the present invention.

Thow U.S. Pat. No. 4,057,065 discloses a percutaneous gastrointestinal tube which is surgically inserted into the patient's stomach and then threaded downward into the intestine. The gastrointestinal tube has two decompression lumens and two inflatable cuffs which appear to comprise the substance of the invention.

Finally, among the more relevant known prior art, U.S. Pat. No. 3,905,361 to Hewson discloses an apparatus for use in artificial respiration and stomach evacuation. The device includes an inflatable member in an elongated aperture portion into which fluid can be introduced or evacuated.

In summary, the present invention features a unique combination of elements which is nowhere disclosed in the prior art whether taken alone or in combination. The device has unique advantages permitting effective gastric lavage at the same time that controlled esophageal tamponade is taking place and thereby facilitating thrombosclerosis during active variceal bleeding. In simpler terms, the device prevents blood to lungs aspiration by the balloon proximal to the end of the tube, the injection site is controlled and the injection to stop bleeding stays where it is. The proximal end cap provides a suction channel which may be used to generate negative pressure within the tube. This facilitates the delivery of varices through the windows. Material can be suctioned from the tube via this suction system. Further, the injection of varices at the level of the esophagogastric junction is as easy as in the more proximal esophagus. Prolonged contact of the sclerosing agent with the wall of the varix can also be achieved.

SUMMARY OF THE INVENTION

The present invention teaches a balloon-tube assembly comprising a multipurpose tamponade and thrombosclerotherapy tube. The tube comprises a transparent polyvinyl tube of predetermined dimensions having a pair of opposing windows in the side wall located approximately 1.5 cm. from its distal end. At a predetermined distance of approximately 5 cm. from these windows, a latex balloon is mounted over the tube and connected to a manometer by means of a polyvinyl catheter having one end with spaced side openings within the balloon. The catheter is bonded to the side of the tube and runs therealong to the proximal end of the tube. The proximal end of the tube is connected to an irrigating system and to a large siphon for gastric drainage. A polyvinyl tube is folded over the proximal end of the tube and a metal cap-thin latex diaphragm fits snugly into the proximal outer tube. It comprises a copper member having a thin latex nipple diaphragm with a small opening which allows the passage of an endoscope. This cap provides a seal to allow gastric air insufflation, yet it is designed to balloon outwardly, leak, or even rupture if there is a sudden increase in intraabdominal pressure. The everted positioned thin latex nipple thus increases the compliance in the system, decreasing the risk of gastric or esophageal injury associated with sudden marked pressure changes seen often as a consequence of gagging. The metal cap also contains an internal channel opening into the main tube and exiting the lateral wall which is connected to suction. The object of the channel is to maintain negative pressure within the main tube which then seals the distal end and delivers varices through the side windows and maintains negative suction even if the suction channel of the endoscope is rendered unusable because of the needle injector being in position or due to blood clots or debris. This channel can also remove secretions in the proximal tube without having to withdraw the endoscope, thus minimizing the length of the procedure.

An object of this invention is to provide a new and improved medical instrument comprising a multipurpose tamponade and thrombosclerotherapy tube.

Another object of this invention is to provide a balloon-tube assembly which permits effective gastric lavage at the same time that controlled esophageal tamponade is taking place, thereby facilitating thrombosclerosis during active variceal bleeding.

A more specific object of this invention is to provide a new and improved medical instrument and method of using same comprising a multipurpose tamponade and thrombosclerotherapy tube having openings at its distal end to permit suction on the blood and washing up through the cap and a balloon catheter arrangement to prevent blood to lungs aspiration and control of the injection site.

BRIEF DESCRIPTION OF THE DRAWINGS

The above and other objects of the invention will be more clearly understood when viewed in conjunction with the accompanying drawings wherein:

FIG. 1 is an elevation view of the tube comprising the invention;

FIG. 2 is a detailed view of the distal end of the tube;

FIG. 3 is a detailed view of the proximal end of the invention;

FIG. 4 is a cross-sectional view taken along the line 4—4 of FIG. 1; and

FIG. 5 is a view of an irrigating and drainage system for coupling to the multipurpose tamponade and thrombosclerotherapy tube to form an integral unit.

DETAILED DESCRIPTION OF THE INVENTION

Referring now to the drawings, the invention comprises a multipurpose tamponade and thrombosclerotherapy tube 10 of a transparent polyvinyl material which in a typical embodiment measures 56 cm. in length. The inner diameter of such tube measures 1.3 cm. and the outer diameter 1.7 cm. A pair of side windows 11a and 11b are located approximately 1.5 cm. from the rounded end 12 of the tubular portion 30. The windows are approximately 0.5 cm. wide by 2.5 cm. long with rounded ends. The windows 11a and 11b are located directly opposite one another in the tube walls or 180° apart.

A latex balloon 13 having a length of approximately 10 cm. is mounted 5 cm. from the inner end of the windows 11a and 11b. The balloon 13 is mounted to the tube 30 by silk ties 14. The balloon 13 is connected to a manometer 15 by means of a catheter 16 of polyvinyl material which is bonded to the tube 10 and includes a plurality of spaced openings 17 within the balloon 13. An inflatable ball 26 or other suitable means are provided in the catheter line 16 to inflate the balloon 13.

A scale 18 with suitable indicia in centimeters is marked along the tube 30 commencing on the proximal side of the balloon 13. The proximal end 19 of the tube 30 is everted and bonded to itself for distance of 1 cm. with the internal diameter being expanded to 2.2 cm. Easily viewed marks are spaced at 90° intervals at the distal end of the tube 30 to permit orientation of the windows relative to the esophageal walls. The dialated proximal end 19 of the outer tube is connected to an irrigating system 20 and to a large bore siphon by means of a T-tube 21 for gastric drainage. The direction of flow is regulated by the use of clamps (not shown).

A metal cap 22 preferably of copper fits snugly into the proximal outer tube 30. The cap 22 has a 1.5 mm. catheter 23 which is connected to a suction system (not shown) by means of a "Y" connector 24. The catheter 23 is used to generate negative pressure within the outer tube assembly. A latex nipple diaphragm 25 is mounted on the cap 22 to provide a seal. The diaphragm has a small opening permitting the passage of an endoscope but preserving an air-tight system.

Typically, the length of the tube can vary from 40 to 95 cm. and the inner diameter can vary from 8 to 25 mm. The balloon can also be mounted at various lengths from the end of the tube 30 and the length of the balloon itself can vary from 2 to 25 cm. Furthermore, the style of windows can vary from 2 to 15 mm. and from 0.5 to 10 cm. The portion of the tube proximal to the balloon 13 can measure from 10 to 80 cm.

The multipurpose tamponade and thrombosclerotherapy tube 10 is designed for many uses. The tube 10 is uniquely effective for an esophageal tamponade, simultaneous gastric lavage and endoscopic variceal sclerosis in both the actively bleeding situation and elective situations. The tube is also effective in the treatment of esophageal variceal tamponade even without variceal sclerosis. The tube 10 may be effectively used for the removal of gastric bezoars and may be used for gastric lavage for drug overdose, accidental poisonings and for foreign object removal for both blunt and sharp materials lodged in the esophagus, stomach or duodenum. The tube 10 is designed to allow efficient gastric lavage in patients with gastrointestinal hemmorrhage while minimizing risks of aspiration. The tube 10 can be used for control of hemorrhage in patients with ulcer disease, Mallory-Weiss tears, or other vascular lesions of the upper intestinal tract. Gastric varices can also be sclerosed with the use of this tube 10.

FIG. 5 illustrates an irrigating and drainage system 20 which is coupled to the multipurpose tamponade and thrombosclerotherapy tube 10. A plastic "T-tube" connector 21 is connected to tube 30 and to a polyvinyl drainage tube 33 approximately 3 to 4 feet in length for flow through the top of the "T" which is normally in an inverted position. A connecting tube 34 with a removable adaptor 35 is mounted to the base of the "T" to permit coupling to a two bottle irrigating system (not shown) under gravity feed.

In a typical application of the invention, an endoscopic procedure is begun after resuscitative steps have been completed with a patient. Local spray anesthesia and titrated sedation with Demerol and/or Valium are used according to the clinical situation. The endoscope is passed through the cap 22 and latex diaphragm 25 and the outer tube 30. The "Y" connector 24 from the suction catheter 23 is taped to the side of the head of the scope. Endoscopy is begun, and the distance from the alveolar ridge to the bleeding varix is measured with the endoscope. The outer tube 30 is then advanced over the endoscope to position the middle of the balloon 13 at the level of the varix. The balloon 13 is rapidly inflated to a pressure of 30-40 mm./Hg., thereby effectively compressing the varix; the endoscope is withdrawn, and the outer tube is connected to the lavage and gravity drainage systems 20. The gastric lavage is begun at the same time that esophageal tamponade is maintained.

After the gastric lavage is completed, the endoscope is advanced into the stomach by sliding the endoscope through the outer tube 30. The outer tube is then sealed with the cap-diaphragm, creating an air-tight system which allows the stomach to be insufflated for complete examination. If there is any doubt concerning the site of bleeding in the esophagus, the outer tube 30 can be quickly withdrawn after deflating the balloon 13 and a relatively clear esophagus is left to be examined.

In thrombosclerosis the endoscope is introduced through the cap 22-diaphragm 25 and the outer tube 30 and advanced to the level of the windows 11a and 11b. The translucency of the tube 30 makes it very easy to identify its segments, to recognize the presence of blood around it, and to orient the tube 30 properly at all times.

Under direct vision, the outer tube 30 with the balloon 13 deflated is moved proximally until the esophagogastric junction is located through the windows 11a and 11b. At this point with slight rotating movements, one or two varices are delivered into the windows 11a and 11b and thrombosclerosis begins. If a flexible needle injector is used, the scope must be removed and the catheter introduced through the biopsy channel. This can be accomplished with antegrade or retrograde feeding of the catheter. When using an Olympus type injector, however, the endoscope does not need to be removed.

The injection of the varix is made with the needle moving parallel to the varix in order to reduce the risk of injection outside the variceal lumen. Prior to the injection, the outer balloon 13 is inflated to a pressure of 20 mm./Hg. in order to minimize blood flow through the paraesophageal varices. Once the needle enters the varix, the pressure in the balloon is increased to 40 mm./Hg., and 1-3 ml. of sclerosing solution is injected. The preferred sequence comprises thrombin followed by sodium morrhuate and Keflin. Special care must be taken not to over distend the varix. The needle is held in place for 30-60 seconds and then withdrawn. If a second varix has been exposed, it is similarly injected. With the needle injector in place, the channel of the scope cannot be used for suction; but negative pressure within the outer tube can be maintained with the attached suction catheter 16. The negative pressure within the outer tube 30 prevents retraction (outside the window) of the varix being injected. The balloon 13 is left inflated for approximately five minutes. If necessary, the tube 30 can be advanced for direct balloon compression of the varix.

Varices up to a level of 33 cm. from the alveolar ridge can be safely injected with this system. To inject more proximal varices the balloon 13 should be kept deflated to avoid inadvertent occulsion of the larynx. With the balloon deflated, the outer tube 30 is removed and the second outer tube with windows 90° apart in relation to the windows of the first outer tube is introduced and the whole procedure is repeated. After the endoscopic thrombosclerosis is completed, the endoscope is introduced into the stomach for a second look. The outer tube is then removed and the esophagus is re-examined as the endoscope is withdrawn.

The use of the outer tube-balloon assembly as described above has several advantages. A major one is that the gastric lavage is carried out at the same time that controlled esophageal tamponade is taking place. The use of a large bore tube for gastric lavage completely eliminates suction artifacts in the gastric mucosa and empties the stomach of all blood clots allowing adequate examination with small scopes. Errors in diagnosis are therefore minimized. Furthermore, the near complete recovery of the lavage solution eliminates worries about fluid or sodium overload in patients with an already frail electrolyte and water balance. The relatively short time needed to completely clear the stomach of blood (8-18 minutes) illustrates the efficiency of this system. Another benefit is the relatively low risk of aspiration, since the balloon 13 prevents fluid from coming up around the outer tube 30.

With the present invention the injection of varices at the level of the esophagogastric junction or the cardia is as easy as in the more proximal esophagus and the cardia can be held in place and the varices at that level delivered through the side windows 11a, 11b with no difficulties. Immobilizing the cardia and esophagus is extremely important in preventing varix displacement and possible laceration during injection, a significant problem in gagging or uncooperative patients.

The use of negative pressure inside the outer tube balloon assembly facilitates the delivery of varices through the side windows 11a, 11b and prevents their retraction at the same time of injection. Injection of the protruding varix minimizes the possibility of mucosal or submucosal injections and should minimize the development of ulcers, strictures or esophageal perforation. Although compression with the outer tube alone can help maintain the sclerosing agent within the injected varix the inflated balloon in this system allows more prolonged stasis. If the injection is initiated with thrombin, a clot will form immediately and will hold the radiopaque material within the injected varix for at least one hour. The sclerosing agent will be held similarly, prolonging its contact with the wall of the varix for better sclerosis. With other techniques, the sclerosant clears rapidly from the varices. The use of the outer tube-balloon assembly also enables improved visualization by eliminating blood from the working field, as well as isolation of the varix to be injected.

In some instances, the pediatric endoscope has been found to be reliable in the evaluation of gastrointestinal bleeding while in other instances it was found inadequate to provide good illumination in the presence of large amounts of blood in the stomach. The use of our tamponade and lavage tube eliminates this potential problem by completely clearing the stomach of blood. The use of the pediatric endoscope allows a small sized outer tube which is easy to pass and less traumatic. The use of a cap-diaphragm in conjunction with suction to generate negative pressure within the outer tube seals all the openings of the tube, preventing the entry of blood or other gastric contents and making it easier to work in a totally clear field. In addition, the large clearance area between the endoscope and the outer tube 30 allows play of the distal tip of the pediatric scope within the outer tube, facilitating controlled injection of the varices. The ease with which the esophagogastric junction is identified through the window allows thrombosclerosis of varices at this level, which in our experience, seems to be the most effective place of injection for control of acute hemorrhage. More proximal injections can also be made if necessary.

The presence of the double window 11a, 11b in the outer tube 30 allows successive injections of two varices, thus saving procedure time. The use of a second outer tube with two windows in different positions assures the opportunity of making four injections at 90° intervals at any level of the esophagus, particularly the esophagogastric junction. Minor rotation of the tube will deliver the desired varix but using only one tube, one would have to rotate it 90° in order to deliver two additional varices. It is rather difficult, however, to maintain the rotation since tube 30 tends to spring back into its original position. Therefore, it is more practical and convenient to use two different soft tubes rather than a single more rigid one. The easily recognizable markings inside the tube allow proper orientation at all times and the centimeter markings in the outer tube allow recording of the precise level of injection.

The outer-tube balloon assembly 10 thus described may be of value in all patients with gastrointestinal bleeding since the use of the assembly 10 allows rapid, effective lavage without production of suction artifacts and with minimal risk of bronchial aspiration. The capping of the proximal end of the tube 30 also permits insufflation and complete endoscopic examination. The tube assembly is particularly suited for high-risk patients.

While the invention has been explained by a detailed description of certain specific embodiments, it is understood that various modifications and substitutions can be made in any of them within the scope of the appended claims which are intended also to include equivalents of such embodiments.

We claim:

1. A multipurpose tamponade and thrombosclerotherapy tube comprising:
    an elongated transparent tube including a closed end and an opposite open end having at least one window aperture in the tube spaced from the closed end thereof, an inflatable balloon mounted over the tube at a spaced interval from the window aperture, a catheter bonded to the tube and extending therealong, said catheter having one end within the balloon and having side openings spaced at intervals along said end within the balloon, a substantially cylindrical cap mounted to said open end of the tube and extending outwardly therefrom and having a catheter coupling opening in the cylindrical wall thereof, and, a flexible nipple diaphragm mounted over the extending open end of said cap, said diaphragm having a closable aperture to permit entry into the tube and provide an effective tube seal said diaphragm further permitting release of pressure in the tube through said aperture.

2. A multipurpose tamponade and thrombosclerotherapy tube in accordance with claim 1 wherein:

the window aperture comprises a pair of directly opposed elongated apertures having rounded end portions with the elongation parallel to the axis of the tube.

3. A multipurpose tamponade and thrombosclerotherapy tube in accordance with claim 2 wherein:

the tube is of polyvinyl material and of uniform diameter, and the open end includes an end portion of enlarged diameter adjacent the open end to receive the cap, said end portion being formed by the tube folded back upon itself for a predetermined distance.

4. A multipurpose tamponade and thrombosclerotherapy tube in accordance with claim 1 further including:

silk ties at each end of said balloon for securing said balloon to the tube, and, means coupled to the catheter for inflating the balloon.

5. A multipurpose tamponade and thrombosclerotherapy tube in accordance with claim 1 wherein:

said tube includes indicia located therealong for determining the position of said tube during use.

6. A multipurpose tamponade and thrombosclerotherapy tube in accordance with claim 1 further including:

an irrigating and drainage system coupled to the open end of said tube, said nipple diaphragm having been removed, said system comprising a "T" tube coupling connected to the open tube, a drainage tube connected in line to the other end of the coupling and an irrigating system connected to the base of the "T" tube.

7. A multipurpose tamponade and thrombosclerotherapy tube in accordance with claim 6 wherein:

the irrigating system includes an adaptor connected into the base of the "T" tube when the irrigating system is not in use.

8. A multipurpose tamponade and thrombosclerotherapy tube in accordance with claim 2 wherein:

the window apertures are each located 1.5 cm. from the closed end of the tube and each measures 0.5 cm. by 2.5 cm. and the inflatable balloon is located 5 cm. from the window apertures along the tube and wherein the tube comprises an inner diameter of 1.3 cm. and an outer diameter of 1.7 cm.

9. A multipurpose tamponade and thrombosclerotherapy tube in accordance with claim 1 further including:

suction means coupled to the catheter opening in the cylindrical cap.

10. The method of performing endoscopic thrombosclerosis for the emergency treatment of bleeding esophageal varices in patients comprising the steps of:

providing an elongated transparent tube having a closed end and an open end with at least one window aperture in the tube spaced from the closed end, an inflatable balloon mounted over the tube at a spaced interval from the window aperture and a catheter bonded to the tube and having an opening within the balloon for inflation purposes and further including a cap and a flexible nipple diaphragm with a sealable aperture mounted over the cap at the open end of said tube, inserting an endoscope through the sealable aperture in the diaphragm and advancing the endoscope to the tube window to view the presence of blood, inflating the balloon to a predetermined pressure to minimize blood flow through the paraesophageal varices, moving the outer tube with the balloon deflated until the esophagogastric junction is located through the window, providing a needle injector for injection of the varix, and delivering one or two varices into the windows with slight rotating movements applied to the tube.

11. The method in accordance with claim 10 wherein:

the pressure in the balloon is increased once the varix injection has been made and said pressure is maintained for a predetermined time interval.

12. The method in accordance with claim 10 further including the steps of:

performing gastric lavage at the same time that controlled esophageal tamponade takes place.

* * * * *

UNITED STATES PATENT AND TRADEMARK OFFICE
CERTIFICATE OF CORRECTION

PATENT NO. : 4,464,175

DATED : August 7, 1984

INVENTOR(S) : Jorge G. Gutierrez and Alan R. Altman

It is certified that error appears in the above—identified patent and that said Letters Patent are hereby corrected as shown below:

On the title page,
The first named inventor of this patent is to be Jorge G. Gutierrez. The second named inventor is to be Alan R. Altman. The patent should be listed as Gutierrez et al.

Signed and Sealed this

Twelfth Day of March 1985

[SEAL]

Attest:

DONALD J. QUIGG

Attesting Officer     Acting Commissioner of Patents and Trademarks